United States Patent [19]
Nokihara et al.

[11] Patent Number: 5,344,613
[45] Date of Patent: Sep. 6, 1994

[54] AGITATION STABILIZER IN SOLID-PHASE PEPTIDE SYNTHESIZER

[75] Inventors: Kiyoshi Nokihara; Rintaro Yamamoto; Makoto Hazama; Shin Nakamura, all of Kyoto, Japan

[73] Assignee: Shimadzu Corporation, Kyoto, Japan

[21] Appl. No.: 9,080

[22] Filed: Jan. 26, 1993

[30] Foreign Application Priority Data

Jan. 29, 1992 [JP] Japan .................. 4-002814[U]

[51] Int. Cl.$^5$ .................. C08F 2/00; C07K 5/00
[52] U.S. Cl. .................. 422/131; 422/62; 422/99; 422/135; 422/312; 435/315; 530/333; 935/88
[58] Field of Search .................. 422/62, 99, 131, 135, 422/143, 312; 435/315, 216; 530/333, 334, 335, 345; 935/88

[56] References Cited

U.S. PATENT DOCUMENTS

| | | | |
|---|---|---|---|
| 3,647,390 | 3/1972 | Kubodena et al. | 422/129 |
| 4,668,476 | 5/1987 | Bridgham et al. | 422/62 |
| 4,746,490 | 5/1988 | Saneii | 422/62 |
| 4,861,866 | 8/1989 | Durrum et al. | 530/333 |
| 4,888,385 | 12/1989 | Hudson | 530/333 X |
| 5,147,608 | 9/1992 | Hudson et al. | 422/63 |
| 5,288,464 | 2/1994 | Nokihara | 422/101 |

FOREIGN PATENT DOCUMENTS 8808872.3  2/1989  Fed. Rep. of Germany.

OTHER PUBLICATIONS

Patent Abstracts of Japn, vol. 13, No. 134, 63-297396, Dec. 5, 1988.

Primary Examiner—Robert J. Warden
Assistant Examiner—Christopher Y. Kim
Attorney, Agent, or Firm—Nikaido Marmelstein Murray & Oram

[57] ABSTRACT

In an automated solid-phase peptide synthesizing apparatus comprising at least one reaction vessel containing particulate resin as an insoluble support matrix which anchors elongating peptide chains yielded through coupling-assembly formation of peptide bonds, mixing agitation of reagents, as well as circulation agitation of washing solvents flushing the coupling-associated reaction solutions, introduced in peptide chain-assembly process steps into the reaction vessel, is effected by the bubbling of an inert gas forcibly passed through the reagents or washing solvent via a drainage port of the reaction vessel, in order to promote peptide synthesis. A removable agitation stabilizer is inserted into the reaction vessel as a barrier for inhibiting extra-vessel escape, due to action of the bubbling inert gas, of the reagents as well as the washing solvents, and of the support matrix anchoring the elongating peptide chains. The stabilizer also breaks clumping and coagulative skinning of elongated peptides bound to the support matrix, as effects further consequent of the action of the bubbling inert gas and levitated thereby toward the mouth of the reaction vessel during peptide synthesis. The stabilizer additionally acts as a baffle furthering mixing agitation, to promote dispersive mixing of the peptidyl resin with the reagents and washing solvents during peptide chain assembly; and It also serves to distribute washing solvents evenly along the inner surface of the reaction vessel.

6 Claims, 5 Drawing Sheets

AGITATION STABILIZER IN SOLID-PHASE PEPTIDE SYNTHESIZER

BACKGROUND OF THE INVENTION

The present invention is directed to solid-phase peptide synthesis; more specifically, it relates to agitation of batches of reaction solutions mixed in amino-acid coupling stages with an insoluble support matrix anchoring growing peptide chains in a solid-phase synthesizing apparatus.

Applications in bioscience for solid-phase peptide synthesis are numerous and include the ready evaluation of peptide synthetic chemistry and of reaction conditions; the study of epitopes, agonists, antagonists or more potent structures; the study of structure-activity relationships; the screening and/or search of peptides to ascertain sequences; as well as the synthetic manufacture of neuropeptides, hormones and antigens.

The product at each stage of synthesis is bound to the insoluble support, and thus can be rapidly filtered and washed. The peptide chain in formation remains anchored to the support in a single vessel in which the peptide chain assembly is carried out, followed by cleavage for purification. This eliminates losses which would otherwise occur owing to the necessity of transferring products in advancing from one stage to the next.

High-efficiency synthesis is desirable, in which highly homogeneous target materials are produced through rapid assembly, reaction time for coupling the amino acids to the growing peptide chain is expedited to suppress the formation of undesired byproducts, and yield approaching quantitative mass recovery is afforded.

In a batch-wise peptide synthesizing procedure, on-going mixing of synthesizing reagents to uniformly disperse the support material within solution batches shortens acylation time and increases efficiency by promoting rapid synthesis, which is thus advantageous for the suppression of byproducts. Alternatively to "continuous-flow synthesis," coupling reaction in batch-wise synthesis is not promoted by means of the recirculation of reagents through the peptide synthesizer reaction vessels, but rather by mixing agitation of synthesizing reagents and washing solvents remaining therein until drained or purged from the vessels.

Batch-wise peptide synthesis involving vortex mixing as a means of promoting peptide coupling is highly effective for mixing during deprotection, coupling and/or washing stages of the synthesizing process. However, mass recovery is poor, because peptidyl resin, i.e. the support material bound with elongating, protected peptide chains, is destroyed by the repetitive vortex mixing, and a portion of the peptidyl resin can then pass through the filter of the reaction vessel. Supersonic or mechanical mixing can also be employed; however these methods also tend to break or to deteriorate the peptidyl resin support material.

Peptide synthesis in which mixing is alternatively effected via bubbling inert gas through the reaction vessel ($N_2$ gas has been used) has been successful for the production of large peptides.

The cycle of batch-wise synthesizing reactions is automated employing a simultaneous, multiple peptide synthesizer recently developed. Peptides can be produced simultaneously in channels of the synthesizer.

The reaction vessel of the automated solid-phase peptide synthesizer has a supply opening, through which batches of reaction solutions are supplied into containment by a reaction chamber defined by the reaction vessel. The chamber contains a suitable support matrix, typically particulate resin, to which the peptide chains in formation are anchored during assembly in peptide synthesis. Both between and following successive N α-deprotecting and coupling steps of the peptide synthesizing assembly procedure, a washing process is carried out, through which excess reagents and undesired products are purged via washing solvents through a drainage port of the vessel. A filter covers the drainage port and sustains the support. The drainage port at the same time serves as an inlet through which inert gas is forcibly introduced into the reaction chamber, in order to effect bubbling agitation.

During the deprotecting and coupling steps, the processes are promoted by the inert gas vigorously bubbled through the reaction chamber of the reaction vessel (the stronger the agitation, the more efficiently are the reagents likely to react with the growing peptide chains). During the subsequent washing process, the bubbling agitation improves washing efficiency as well. The support material and reagents, and the washing solution therein are, however, liable to splash out from the reaction chamber.

During peptide chain assembly, flocculation leading to clumping and coagulative skinning of the protected peptidyl resin can arise, due perhaps to interaction, among the peptide chains, of side chain aromatic rings with their protecting groups; to steric hindrance of the deprotected terminal ends of the coupling amino acids; and/or to hydrogen-bonding. This tendency becomes especially pronounced wherein peptide chains ten to fifteen amino acids or longer are synthesized, despite the action of the inert gas bubbling as a mixing agency. Moreover, the bubbling agitation, as it is increasingly vigorous, levitates the floc within the reaction chamber, such that clumped or skinned peptidyl resin is eventually compelled to break without it. This phenomenon impairs the consistency of the coupling reaction, and lowers the peptide yields.

Simply reducing the intensity of the inert gas bubbling will curb splashing of the reaction solutions and flocculation of the resin binding protected peptides. Agitation not vigorous enough can impair the coupling processes rather than promote their efficiency, however, since with low-level bubbling requiring correspondingly longer reaction time, reactions do not progress completely, defective peptides are produced and sub-reactions occur, increasing the risk that undesired by-products or deletion peptides may form, and defeating the product homogeneity and reaction efficiency sought therein.

Another alternative might be to cap the reaction vessel, but such a cap would have to be perforated in order to allow the bubbling gas to escape, which perforations would again permit the extra-vessel escape of reaction solutions or resin-particulate anchored peptides, as carried by the bubbles. Moreover, such a cap would not be effective in inhibiting or breaking the effects of the above-described flocculation, nor in bringing about more efficient mixing of the reaction solutions bathing the support.

The reagents and washing solvents of each batch of reaction solutions during a peptide synthesizing procedure are supplied through the feed tip of a tube inserted into the reaction vessel supply opening, flush with the reaction chamber so as to obviate retention of the synthesizing reagents due to capillarity at the feed tip following supply. It is desirable, however, that when washing solvent is supplied, it is distributed evenly along the cylindrical surface of the reaction chamber, in order to wash it completely of reaction solution.

SUMMARY OF THE INVENTION

An object of the present invention is to improve the efficiency of peptide synthesis in a solid-phase peptide synthesizing apparatus, producing residues of high homogeneity, at yield approaching mass recovery.

Another object is to inhibit extra-vessel escape of reaction solutions, and of resin bound with protected elongated peptides, from reaction vessels of a peptide synthesizing apparatus, due to action of bubbling inert gas employed therein to promote amino acid coupling and deprotecting of N α groups prior to coupling.

A further object of the present invention is to break clumping and coagulative skinning of the peptide-bound resin, due to flocculation effects abetted by the action of the bubbling inert gas, and levitated thereby toward the mouth of the reaction vessel during peptide synthesis.

A further object is ensure accuracy in the feeding of peptide-synthesizing reagents and to improve thoroughness in the feeding of washing solvents into the reaction vessel of an automated peptide synthesizer.

A solid-phase peptide synthesizing apparatus according to the present invention promotes peptide synthesis by bubbling an inert gas through an insoluble support anchoring protected peptide chains in coupling formation, bathed by reagents. The solutions for the coupling reaction are contained in reaction chambers each defined by a reaction vessel comprising a channel of the apparatus. Between coupling stages, N α protecting groups are temporarily removed, before and after which process the peptide chains and reaction chamber are cleansed by washing solvents, also bubbled therein by the inert gas. The solutions are purged through a drainage port of the reaction vessel, which port serves as an inlet for the pressurized introduction of the inert gas into the reaction chamber. The insoluble support typically comprises particulate resin and is sustained within the reaction chamber on a filter covering the drainage port.

A removable stabilizer is installed into the reaction chamber, therein inhibiting splash of the reaction solutions arising from the bubbling agitation effected by the inert gas passed through the chamber. The stabilizer also serves to break clumping and coagulative skinning of the peptide-bound resin, due to flocculation effects abetted by the action of the bubbling inert gas, and raised in the reaction chamber toward a reaction solution supply opening of the reaction vessel, under agency of the bubbling gas.

The stabilizer additionally acts as a baffle to further the effectiveness of mixing agitation, promoting dispersive mixing of the peptidyl resin with the reagents and washing solvents during peptide chain assembly. Furthermore, the upper portion of the stabilizer is annular, corresponding with the cylindrical surface of the reaction chamber. The stabilizer thus effects circular distribution of the reagents and, in particular, of the washing solvents along the reaction chamber wall.

The foregoing and other objects and advantages of the present invention will be more fully apparent from the following detailed description.

DESCRIPTION OF THE PREFERRED EMBODIMENT

Figure 1:
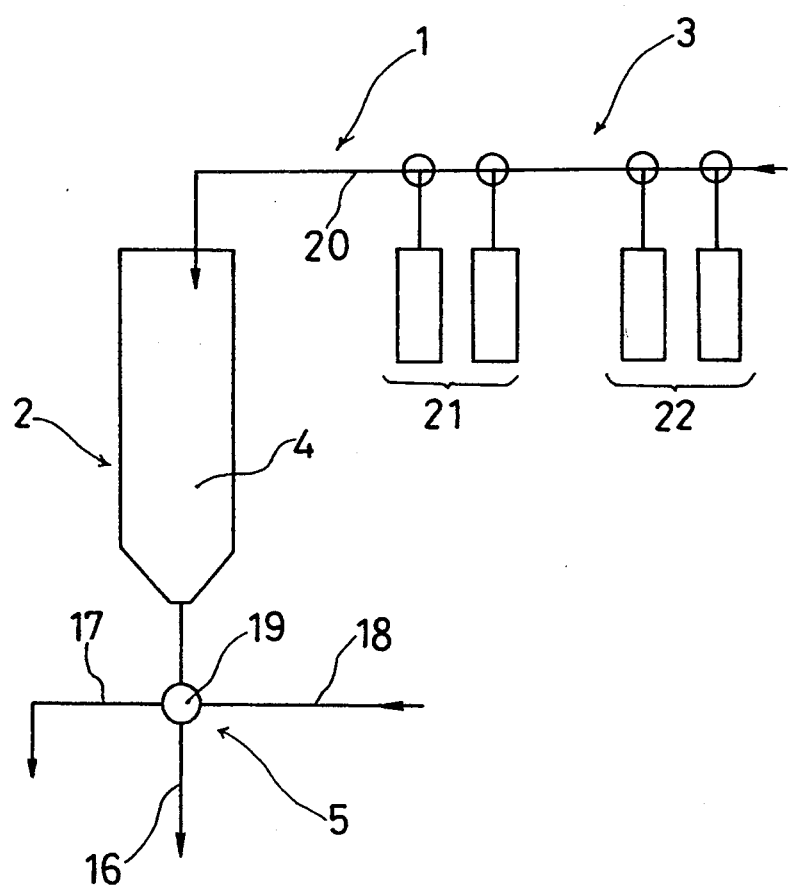
FIG. 1 is a schematic diagram illustrating a reaction device and associated elements composing a reaction assembly according to the present invention, for peptide synthesis in a solid-phase peptide synthesizing apparatus.

The principal components of the reaction assembly 1, as shown in FIG. 1, of a solid-phase peptide synthesizing apparatus are a reaction device 2 and a reaction solution supplier 3. The reaction device 2 consists chiefly of a reaction vessel 4, outfitted according to the present invention, and a collection device 5.

Figure 2:
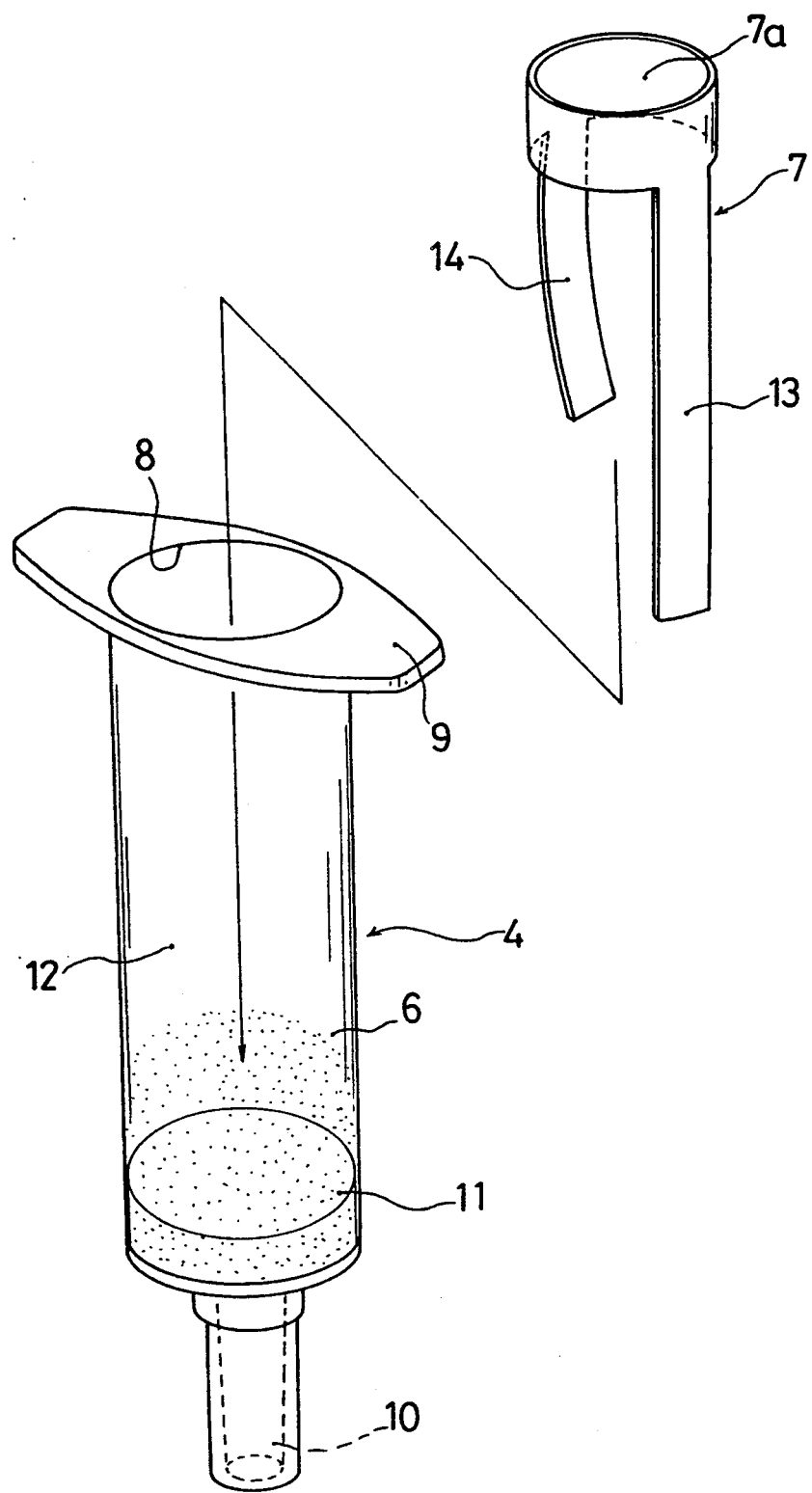
FIG. 2 is a perspective view of the reaction vessel, further showing in exploded view an agitation stabilizer according to the present invention.

FIG. 2 illustrates the component parts of the reaction vessel 4: an approximately cylindrical vessel body 6, one end of which is a supply opening 8 rimmed by a flange 9, and projecting from the other end of which is a drainage port 10. A stabilizer 7, is shown in exploded view in FIG. 2. The vessel body 6 is made of a substance which is not chemically reactive with the insoluble support, described in the following, and which scarcely generates static electricity. Polypropylene is an example of a suitable material which is inexpensive, and is minimally adsorbent of synthesized peptide.

A filter 11 is provided in the end of the vessel body 6 over the drainage port 10. The filter 11 separates a reaction chamber 12 defined by the vessel body 6 from the drainage port 10. The filter 11 is made from a suitable porous material, e.g. a polyalkylene polymer such as polypropylene, polyethylene etc., polypropylene herein being the most preferable.

The stabilizer 7 consists of an annulus 7a, and a support leg 13 and a baffle leg 14 extending downwards in the figure from the annulus 7a. The outer diameter of the annulus 7a is slightly smaller than the inner diameter of the reaction chamber 12. The support leg 13 and baffle leg 14 are integral with the annulus 7a and are diametrically opposed. The length of the baffle leg 14 is about half of that of the support leg 13, and it is bent toward the latter. The stabilizer 7 is inserted into the reaction chamber 12, containing the support, which herein is a particulate resin initially in powdered form, sustained on the filter 11. Therein the leg 13 penetrates the resin support, resting on the filter 11 and standing the stabilizer 7 within the reaction chamber such that the curved baffle leg 14 is suspended over the resin support.

Figure 3:
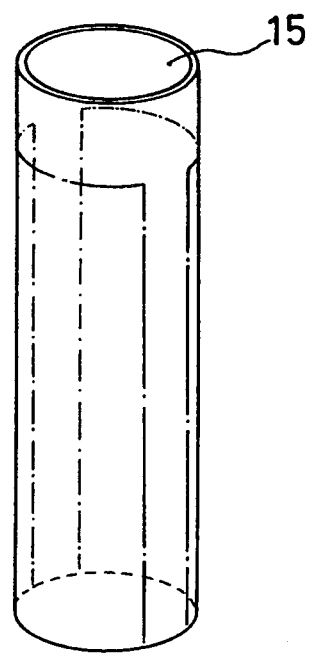
FIG. 3 is a perspective view of a tube of stock material, indicating a method of procuring an agitation stabilizer.

The stabilizer 7 is reusable, and is manufactured from a polymer material such as polypropylene or fluorocarbon polymer ("Teflon"). "Teflon" is preferable. The stabilizer 7 is fabricated from a stock tube 15 as shown in FIG. 3. The tube 15 is cut as indicated along the dotted lines to form a pair of legs, and then one of the legs is cut in half lengthwise and bent toward the other leg.

The collection device 5 indicated in FIG. 1 is detachably connected to the drainage port 10 of the reaction vessel 4, and has a drainage path 16, a collection path 17 and a gas supply path 18. Provided at the junction of the paths 16, 17 and 18 is a directional control valve 19 which changes flow direction in the vessel via which of the paths 16–18 is connected with the drainage port 10. The other end of the gas supply path 18 is connected to a (not shown) inert gas supply.

Extending from the reaction solution supplier 3 is a reaction solution supply path 20 which supplies reagents and washing solution through a tube a feed tip of which is inserted slightly into the reaction vessel 4 through the supply opening 8, wherein it is contiguous with the reaction chamber 12, so as to obviate retention, due to capillarity at the feed tip, of the reaction solutions after supply. Connected midway along the reaction solution supply path 20 are a plurality of reagent tanks 21 containing the batches of reagents used in the coupling stages of the peptide synthesis, and a plurality of washing solution tanks 22 containing the washing solutions used both for washing out the reaction vessel 4 itself, and for washing the peptide product produced by each batch in the coupling procedure and sustained on the filter 11; wherein the elongating protected peptides remain bound to the resin particulates until the final product is cleaved for purification. The remaining end of the reaction solution supply path 20 is connected to the inert gas supply.

A batch-wise coupling peptide-synthesis method pertaining to the embodiment of the present invention will now be described.

Figure 4:
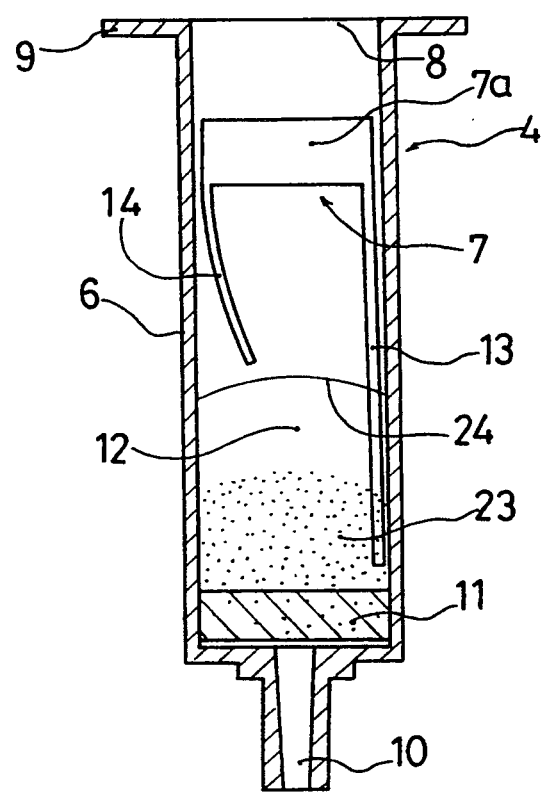
FIG. 4 is a view of the reaction vessel in cross-section.

First, a quantity of powdered particulate resin 23 is supplied into the reaction chamber 12 of reaction vessels 4 corresponding to channels of the peptide synthesizing apparatus, wherein the resin support 23 rests on the filter 11 over the drainage port 10 of the reaction vessel 4, as illustrated in FIGS. 2 and 4. The stabilizer 7 is then installed into the reaction chamber 12 such that the support leg 13 penetrates the resin support 23 to rest on the filter 11, standing the annulus 7a of the stabilizer 7 concentrically within the reaction chamber 12, wherein the baffle leg 14 does not interfere with the resin support anchoring peptide chains in coupling formation during peptide synthesis.

A solution of coupling reagents, or a mixture of preactivated acylcomponent (generally, protected amino acid) and dimethylformamide (DMF) solvent, is then supplied into the reaction chamber 12 via the supply path 20 from the reagent tanks 21, according to a protocol of the peptide synthesizing apparatus. In subsequent deprotecting and coupling steps, inert gas, e.g. $N_2$ gas, is forcibly introduced into the reaction chamber 12 through the gas supply path 18 and the drainage port 10 into the reaction chamber 12, regulated by the valve 19 of the collection device 5 according to the protocol. The supplied inert gas spouts out from the filter 11, bubbling the reagent solution as well as the resin support 23 anchoring the peptides in formation as contained in the reaction chamber 12.

Following elapse of time sufficient to allow peptide coupling to take place, during which the coupling process in the solution batch is promoted by the bubbling-gas agitation, the reagent is purged from the reaction chamber 12 through the filter 11, the drain port 10 and the drain path 16, by agency of inert gas delivered opposite the bubbling-agitation direction, through the supply path 20 into the reaction chamber 12, wherein coupled peptides constituting forming peptide chains remain anchored to the resin support 23 sustained in the reaction chamber 12 by the filter 11.

Washing solvent is supplied during the washing processes into the reaction chamber 12 through supply opening 8, via the supply path 20 from the washing solution tanks 22, further according to the protocol. $N_2$ gas is again forcibly introduced into the reaction chamber 12 through the drainage port 10, as a circulating agent promoting washing of the resin binding elongated peptides in coupling formation. Likewise, the reaction chamber 12 is purged of the washing solvent through the drainage port 10 when communicated with the drainage path 16 via the directional control valve 19. The peptide chains elongating in coupling assembly remain bound to the resin support 23 sustained on the filter 11.

In contrast, other, ordinary methods would involve employing a hollow needle having a filter at the tip in order to suck up excess washing solution, or supernatant left after precipitation of the peptide product upon cleaving for purification.

During the coupling processes in peptide synthesis, flocs forming a coagulative skin 24, as indicated in FIG. 4, as well as clotted or aggregated clumps of the resin support 23 anchoring the growing peptide chains (i.e., elongated peptidyl resin) when bathed in either the reagent or washing solutions, may arise in the reaction chamber 12, abetted by the bubbling action of the inert gas. The coagulative skin 24 or clotted/aggregated clumps are levitated toward the supply opening 8 as the pressure in the chamber increases due to the supplied gas, but are broken when risen into contact with the end of the baffle leg 14 of the stabilizer 7. Furthermore, splash of the reagent or washing solution containing the resin support 23 anchoring peptide chains, inasmuch as bubbling the skin 24 or clumps compels the materials out from the supply opening 8, is prevented by the stabilizer 7 in its configuration.

Accordingly, as described in the foregoing, the resin support 23 and the reaction solution batches associated with peptide coupling in the synthesis stages are securely contained against extra-vessel escape within the reaction chamber 12, ensuring proper proportions of the reagents are maintained for maximum yields. Containment by the stabilizer the rein furthermore allows delivery of the bubbling inert gas at increased pressure, so as to effect maximum efficiency of mixing agitation, unhindered by side effects of flocculation. Thus in comparison with conventional methods, higher yields nearer quantitative mass recovery of highly homogeneous (99% yields for example) peptide product are achieved.

Modification

Figure 5:
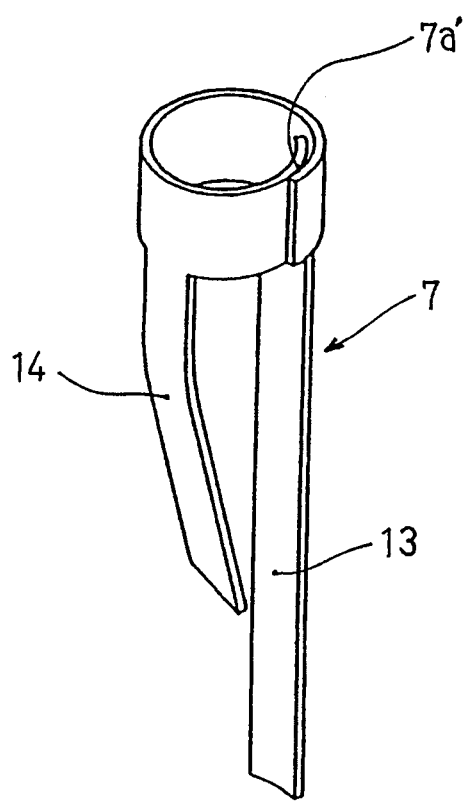
FIG. 5 is a perspective view of a modification of the agitation stabilizer shown in FIG. 2.

An agitation stabilizer directed to peptide synthesis according to the present invention can be modified as shown in FIG. 5. The stabilizer is procured from a stock tube cut to form an overlapping break along the tube wall. The baffle and support legs are formed likewise as in the foregoing; but the resulting annulus 7a' of the modified stabilizer is formed thus with an overlapping break, which acts as a baffle to further promote dispersive mixing of the resin support with the coupling reaction solutions, and to break peptidyl resin floc.

Additional Embodiment

Figure 6:
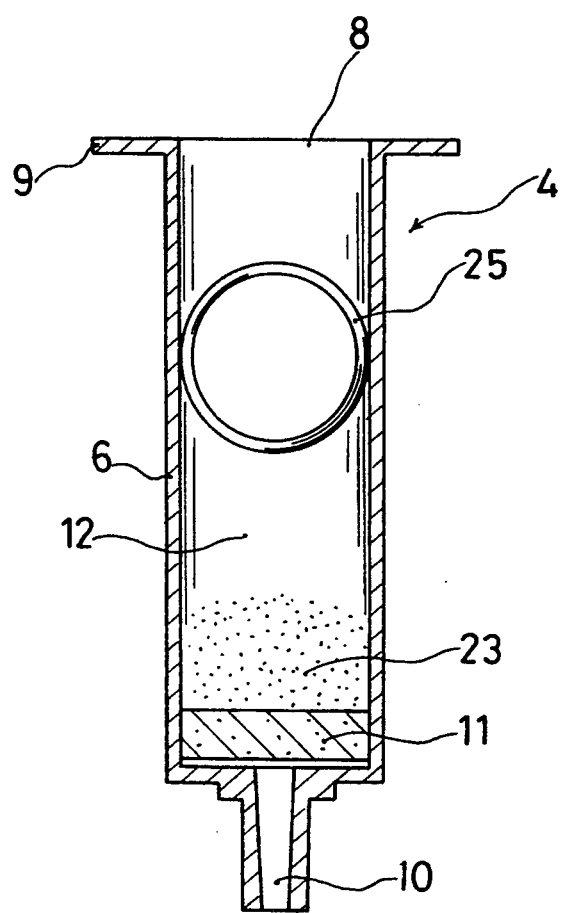
FIG. 6 is a view of the reaction vessel in cross-section, showing contained therein another embodiment of an agitation stabilizer according to the present invention.

Another embodiment according to the present invention is illustrated in FIG. 6. The embodiment comprises an O-ring 25 removably installed into the reaction vessel 4 such that in the planar direction of the ring, it is situated vertically within the reaction chamber 12, at sufficient distance from the supply opening 8 such that checked splash and floc as described in the foregoing are not conducted out of the vessel by the O-ring itself. Benefits effected are likewise as those achieved through the above described embodiment.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. A solid-phase peptide synthesizing apparatus, wherein peptide synthesis is promoted by means of bubbling agitation of reagents and washing solvents bathing an insoluble support matrix which anchors elongating peptide chains yielded through coupling-assembly formation of peptide bonds, comprising:
    a reaction vessel having a drainage port, through which inert gas is forcibly introduced into a reaction chamber within said reaction vessel, in order to effect said bubbling agitation, said reaction vessel having further a supply opening, through which said reagents and said washing solvents are supplied into the reaction chamber, said reaction chamber further containing an insoluble support matrix sustained on a filter covering said port; and
    a stabilizer removable from said reaction chamber positioned within said reaction chamber, for inhibiting splash of said reagents and washing solvents arising from said bubbling agitation, and further for breaking clumping and coagulative skinning of peptide-bound support matrix, due to flocculation effects abetted by said bubbling agitation during said coupling assembly of peptide chains, and levitated thereby in said reaction chamber;
    said reaction vessel defining said reaction chamber being substantially cylindrical;
    said stabilizer being partially formed as an annulus of diameter so corresponding to said reaction chamber as to allow said stabilizer to be concentrically accommodated within said reaction chamber;
    said annulus of said stabilizer being supported by a leg in extension therefrom; and
    said annulus also having a baffle leg in extension likewise as but shorter than said support leg, and bent radially inward relative to said annulus, for breaking clumping and coagulative skinning of said peptide-bound support matrix, due to said flocculation effects; wherein said baffle leg further promotes dispersive mixing, of said insoluble support matrix anchoring forming peptide chains with said reagents and washing solvents, during said peptide chain coupling assembly.

2. A solid-phase peptide synthesizing apparatus according to claim 1, wherein said stabilizer is positioned so as to avoid interference with the supply of said reagents and washing solvents thereinto; said stabilizer furthermore being configured so as to avoid interference with said supply.

3. A solid-phase peptide synthesizing apparatus according to claim 1, wherein said stabilizer support leg in installation penetrates said insoluble support matrix and is adjacent said filter within said reaction chamber.

4. A solid-phase peptide synthesizing apparatus according to claim 3, wherein said supply of said reagents and washing solvents is through a tube a feed tip of which is contiguous with the reaction chamber near the supply opening of said reaction vessel, so as to obviate retention, due to capillarity at said feed tip, of said reagent or washing solvent after supply; wherein further
    said annulus of said stabilizer effects circular distribution of said reagents and said washing solvents along said reaction chamber, thereby enhancing cleaning of said reaction chamber by said washing solvents.

5. A solid-phase peptide synthesizing apparatus according to claim 1, wherein said stabilizer is configured as an O-ring, and is removably installed into the reaction chamber such that said O-ring, in a planar direction therethrough, is substantially parallel to the reaction chamber axially.

6. In an automated solid-phase peptide synthesizing apparatus comprising at least one reaction vessel containing an insoluble support matrix for anchoring elongating peptide chains yielded through coupling-assembly formation of peptide bonds, and means for effecting mixing agitation of reagents and circulation agitation of washing solvents introduced in peptide chain coupling-assembly process steps into said reaction vessel through a mouth thereof, wherein an agitating material is forcibly passed through said reagents and washing solvents, via a drainage port provided in said reaction vessel, in order to promote both deprotecting reactions and peptide bond formation in said coupling assembly process, an improvement which comprises:
    a stabilizer removable from said reaction chamber positioned within said reaction vessel such that said stabilizer acts as a barrier for inhibiting extra-vessel escape, due to action of said agitating material, of said reagents and said washing solvents, and of said insoluble support matrix anchoring said peptide chains elongating through said coupling assembly; and further for breaking clumping and coagulative skinning of peptide-bound support matrix, due to flocculation effects abetted by action of said agitating material therein and compelled thereby toward the mouth of said reaction vessel during said peptide chain coupling-assembly process; and wherein said stabilizer is so configured as to avoid interference with the introduction into said reaction vessel of said reagent and said washing solvent through said mouth thereof, and further so as to promote dispersive mixing, of said insoluble support matrix anchoring said elongating peptide chains with said reagents and washing solvents, during said peptide chain coupling-assembly process;
    said reaction vessel defining said reaction chamber being substantially cylindrical;
    said stabilizer being partially formed as an annulus of diameter so corresponding to said reaction chamber as to allow said stabilizer to be concentrically accommodated within said reaction chamber;
    said annulus of said stabilizer being supported by a leg in extension therefrom; and
    said annulus also having a baffle leg in extension likewise as but shorter than said support leg, and bent radially inward relative to said annulus, for breaking clumping and coagulative skinning of said peptide-bound support matrix, due to said flocculation effects; wherein said baffle leg further promotes dispersive mixing, of said insoluble support matrix anchoring forming peptide chains with said reagents and washing solvents, during said peptide chain coupling assembly.

* * * * *